United States Patent
US 12,023,660 B1
Adam et al.
Jul. 2, 2024

(54) METHOD OF FORMING METAL OXIDE NANOSTRUCTURES ON A TiO$_2$-ZnO-BUFFERED SUBSTRATE

(71) Applicant: King Faisal University, Al-Ahsa (SA)

(72) Inventors: Mohamed Shaker Sayed Adam, Al-Ahsa (SA); Amel Musa Taha, Al-Ahsa (SA); Mohamed M. Makhlouf, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/534,147

(22) Filed: Dec. 8, 2023

Related U.S. Application Data

(62) Division of application No. 18/110,525, filed on Feb. 16, 2023.

(51) Int. Cl.
 *B01J 21/06* (2006.01)
 *B01J 23/06* (2006.01)
 (Continued)

(52) U.S. Cl.
 CPC ......... *B01J 31/2217* (2013.01); *B01J 21/063* (2013.01); *B01J 23/06* (2013.01);
 (Continued)

(58) Field of Classification Search
 CPC ...... B01J 21/063; B01J 23/06; B01J 35/0013; B01J 37/0221; B01J 37/0228;
 (Continued)

(56) References Cited

U.S. PATENT DOCUMENTS 6,645,444 B2 * 11/2003 Goldstein ............ B01J 31/2208 977/777
7,413,725 B2 * 8/2008 El-Shall ................ B22F 9/12 502/343

(Continued)

FOREIGN PATENT DOCUMENTS

WO 2022144043 A1 7/2022

OTHER PUBLICATIONS

Bethelanucha et al., "Immobilized TiO2/ZnO Sensitized Copper (II) Phthalocyanine Heterostructure for the Degradation of Ibuprofen under UV Irradiation," Separations, 8(3): pp. 24(2021).

(Continued)

*Primary Examiner* — Cam N. Nguyen
(74) *Attorney, Agent, or Firm* — Nath, Goldberg & Meyer; Richard C. Litman

(57) ABSTRACT

A method of forming TiO$_2$—ZnO nanoparticles coated by a copper (II) complex includes forming a mononuclear copper complex by treating a ligand with Cu$^{2+}$ ions; and immobilizing the mononuclear copper complex on TiO$_2$—ZnO nanoparticles to obtain the TiO$_2$—ZnO nanoparticle coated by the copper (II) complex. The TiO$_2$—ZnO nanoparticles coated by a copper (II) complex thus produced have improved catalytic effectiveness and increased efficiency by reducing catalytic reaction time and temperature, particularly in methods of catalyzing oxidation of an alcohol or of catalyzing decarboxylative bromination of an acid.

8 Claims, 7 Drawing Sheets

(51) Int. Cl.
  *B01J 31/22*    (2006.01)
  *B01J 31/38*    (2006.01)
  *B01J 35/00*    (2024.01)
  *B01J 35/23*    (2024.01)
  *B01J 37/02*    (2006.01)
  *B01J 37/03*    (2006.01)
  *B01J 37/04*    (2006.01)
  *B01J 37/34*    (2006.01)
  *C07C 45/29*    (2006.01)
  *C07C 51/295*   (2006.01)

(52) U.S. Cl.
  CPC .............. *B01J 31/38* (2013.01); *B01J 35/23* (2024.01); *B01J 37/0221* (2013.01); *B01J 37/0228* (2013.01); *B01J 37/0244* (2013.01); *B01J 37/035* (2013.01); *B01J 37/04* (2013.01); *B01J 37/343* (2013.01); *C07C 45/29* (2013.01); *C07C 51/295* (2013.01); *B01J 2231/40* (2013.01); *B01J 2231/763* (2013.01); *B01J 2531/004* (2013.01); *B01J 2531/16* (2013.01)

(58) Field of Classification Search
  CPC ...... B01J 37/0244; B01J 37/035; B01J 37/04; B01J 37/343; B01J 31/2217; B01J 31/38; C07C 45/29; C07C 51/295
  See application file for complete search history.

(56) References Cited

U.S. PATENT DOCUMENTS

| | | | | |
|---|---|---|---|---|
| 7,622,421 | B2* | 11/2009 | Deevi | A24B 15/18 |
| | | | | 502/343 |
| 8,609,121 | B2* | 12/2013 | Averett | B01J 23/06 |
| | | | | 502/343 |
| 8,623,220 | B2* | 1/2014 | Bagabas | B01J 35/23 |
| | | | | 502/343 |
| 9,055,751 | B2* | 6/2015 | Averett | B01J 23/06 |
| 9,144,242 | B2* | 9/2015 | Averett | B01J 35/40 |
| 9,392,795 | B2* | 7/2016 | Averett | B01J 35/393 |
| 9,873,115 | B2* | 1/2018 | Nagpal | B01J 35/39 |
| 10,279,393 | B2* | 5/2019 | Reed | B01J 35/23 |
| 11,045,793 | B1* | 6/2021 | Soliman | B01J 37/04 |
| 11,826,742 | B1* | 11/2023 | Adam | B01J 23/06 |
| 2023/0219066 | A1* | 7/2023 | Bai | B01J 23/72 |

OTHER PUBLICATIONS

Alattar et al., "Synthesis, characterization and study the photodecolorization of Schiff base Fe(III) complex in ZnO/Uv-A light system," AIP Conference Proceedings, Dec. 2020.

Yesmin et al., "Synthesis, Characterization and Investigation of Antimicrobial Activity of a New Schiff Base, 2-(((2- ((4-hydroxybenzylidene) amino)ethyl)imino)methyl) Phenol and Its Cu(II) and Ni(II) Complexes," Asian Journal of Chemical Sciences, 7(2):30-38, Mar. 2020.

* cited by examiner

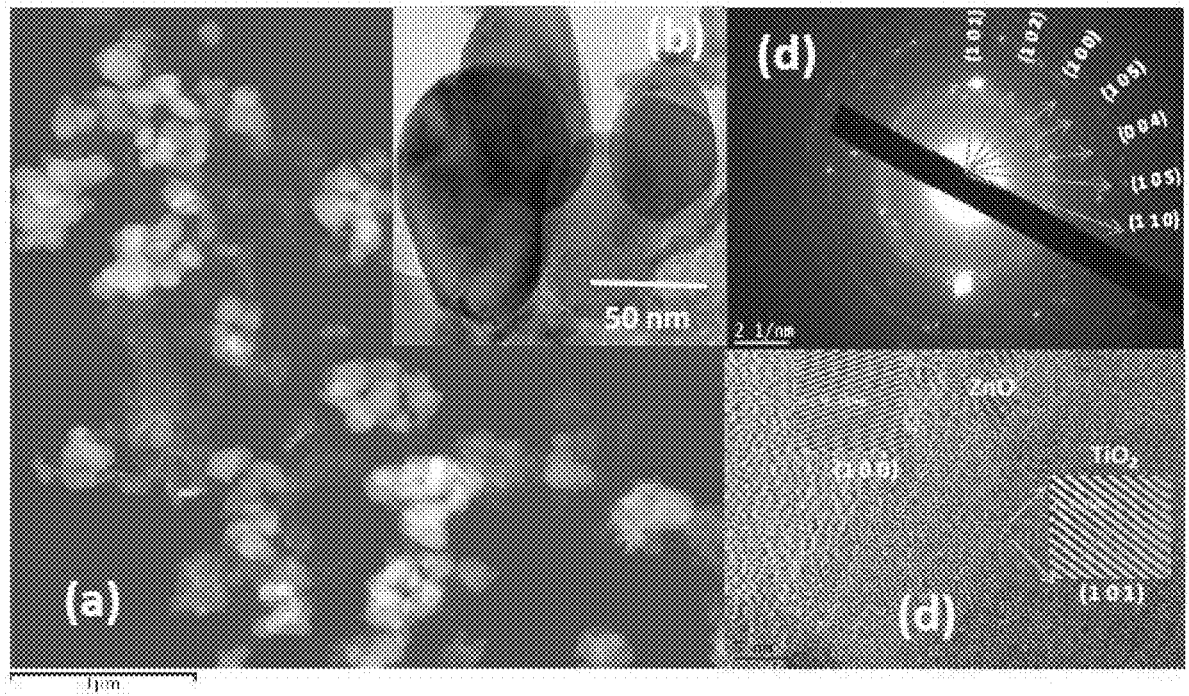
FIGS. 5A-D
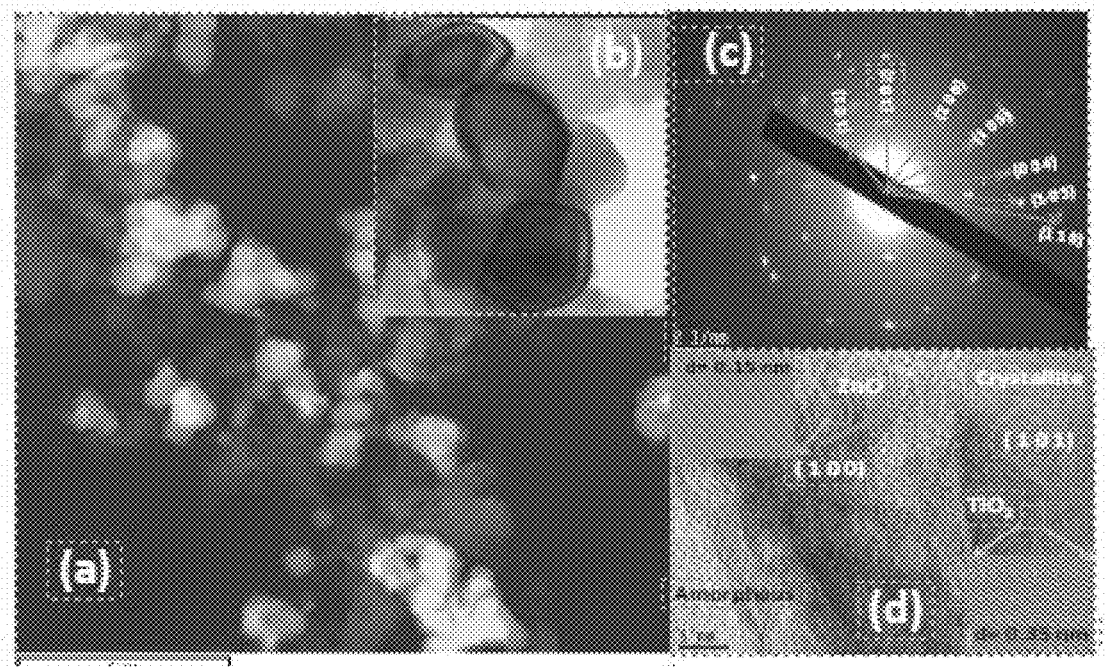
FIGS. 6A-D

METHOD OF FORMING METAL OXIDE NANOSTRUCTURES ON A TiO$_2$-ZnO-BUFFERED SUBSTRATE

CROSS-REFERENCE TO RELATED APPLICATION

This application is a divisional of U.S. patent application Ser. No. 18/110,525, filed on Feb. 16, 2023.

BACKGROUND

1. Field

The disclosure of the present patent application relates to TiO$_2$—ZnO nanoparticles coated by a copper (II) complex and methods of making such nanoparticles. The thus produced nanoparticles have improved catalytic effectiveness and increased efficiency.

2. Description of the Related Art

Despite the high catalytic efficiency of transition metal-complex catalysts, as homogeneous catalysts, compared to those of their heterogeneous analogues, their recoverability, reusability, temperature stability, and high separability in catalytic systems is difficult. Accordingly, immobilization and support of transition metal-complex catalysts on inorganic materials, e.g., Fe$_3$O$_4$, TiO$_2$ and SiO$_2$, by conversion of their features from the homogeneous to the heterogeneous phase could improve their physicochemical characterization. The most important significant property for the heterogeneous catalysts is the evolution specific surface area, e.g., Fe$_3$O$_4$ nanoparticles as TiO$_2$@Fe$_3$O$_4$ and SiO$_2$@Fe$_3$O$_4$.

Nanoparticles of transition metal oxides, e.g., ZnO, have been attracting more attention with their versatile application due to their non-toxicity, low cost of synthesis and non-hygroscopic shape. ZnO is used in certain industrial demands, e.g., as photocatalysts in the selective oxidation of alcohols and as am ultrasound assisted ZnO catalyst in benzyl alcohol oxidation. Its catalytic effectiveness was improved through the combination with doped metals, e.g., CuO—ZnO, CuZnO and FeZnO. TiO$_2$—ZnO as mixed metal oxides has been reported as a successful catalyst for the fabrication of biodiesel. In particular, TiO$_2$ has been shown to be a substantial doped metal oxide for supporting other nonstructural particles, e.g., Fe$_3$O$_4$ and ZrO$_2$, and CuO, due to its significant characteristics of cost effectiveness, remarkable biological uses, nontoxicity and facial preparation.

Catalytic reactivity of the metal oxide catalysts is influenced by the nature of both the central metal ions and the coordinated ligands. The effect of the central metal ion could be observed within its ability to approach the reacting components to achieve the catalytic processes to the selective productivity. For example, most catalytic oxidation reactions of alcohols, especially benzyl alcohol, need high reaction temperatures (50-90° C.) and take a longer than desired time (3-7 h).

Thus, a low-temperature, more cost- and energy-effective method of forming metal oxide nanostructures solving the aforementioned problems is desired.

SUMMARY

The present subject matter relates to a low-cost copper (II) Schiff base-complex immobilized on TiO$_2$—ZnO nanoparticles, namely a Cu-complex@TiO$_2$—ZnO, as a heterogeneous catalyst.

In one embodiment, the present subject matter relates to a method of forming a TiO$_2$—ZnO nanoparticle coated by a copper (II) complex, comprising: forming a mononuclear copper complex by treating a ligand with Cu$^{2+}$ ions; and immobilizing the mononuclear copper complex on TiO$_2$—ZnO nanoparticles to obtain the TiO$_2$—ZnO nanoparticle coated by the copper (II) complex.

In an embodiment, the TiO$_2$—ZnO nanoparticles coated by a copper (II) complex prepared by this method have a ZnO core surrounded by the TiO$_2$, wherein the copper (II) complex is immobilized on the TiO$_2$.

In another embodiment, the present subject matter relates to a method of catalyzing oxidation of an alcohol, the method comprising: contacting the TiO$_2$—ZnO nanoparticle coated by a copper (II) complex with the alcohol in the presence of aqueous H$_2$O$_2$ or tBuOOH; and obtaining a corresponding aldehyde and acid.

In a further embodiment, the present subject matter relates to a method of catalyzing decarboxylative bromination of an acid, the method comprising: contacting the TiO$_2$—ZnO nanoparticle coated by a copper (II) complex herein with the acid and a bromide in the presence of aqueous H$_2$O$_2$ or tBuOOH; and obtaining a corresponding decarboxylated acid.

These and other features of the present subject matter will become readily apparent upon further review of the following specification and drawings.

BRIEF DESCRIPTION OF THE DRAWINGS

FIGS. 5A-D show a HRTEM image of the TiO$_2$—ZnO nanocomposite (FIG. 5A), a high magnification HRTEM image of the TiO$_2$—ZnO nanocomposite (FIG. 5B), a SEAD pattern of the TiO$_2$—ZnO nanocomposite (FIG. 5C), and a d-spacing image of the TiO$_2$—ZnO nanocomposite (FIG. 5D).

FIGS. 6A-D show a HRTEM image of the Cu-complex@TiO$_2$—ZnO (C-T-Z) nanocomposite (FIG. 6A), a high magnification HRTEM image of the C-T-Z nanocomposite (FIG. 6B), a SEAD pattern of the C-T-Z nanocomposite (FIG. 6C), and a d-spacing image of the C-T-Z nanocomposite (FIG. 6D).

Similar reference characters denote corresponding features consistently throughout the attached drawings.

DETAILED DESCRIPTION OF THE PREFERRED EMBODIMENTS

Figure 1A:
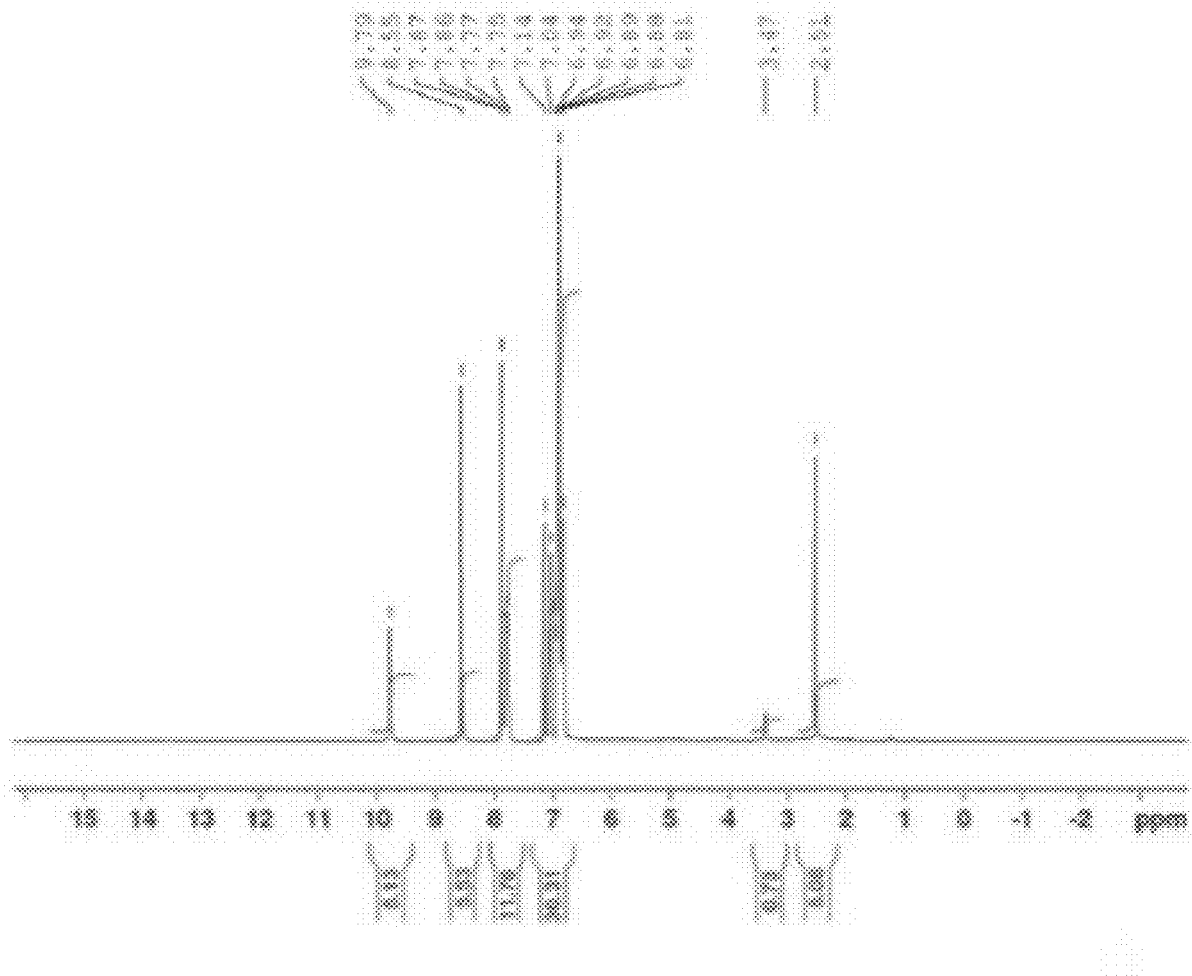
FIG. 1A is an $^1$HNMR spectra of the Schiff base ligand 2-((4-hydroxybenzylidene)amino)phenol in DMSO-d6 at 25° C.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a low-cost copper (II) Schiff base-complex immobilized on $TiO_2$—ZnO nanoparticles, namely a Cu-complex@$TiO_2$—ZnO, as a heterogeneous catalyst. In an embodiment, the Cu-complex@$TiO_2$—ZnO catalytic reactivity was effective in the oxidation of benzyl alcohol and for the decarboxylative bromination of α,β-cinnamic acid by an aqueous $H_2O_2$.

In one embodiment, the present subject matter relates to a method of forming a $TiO_2$—ZnO nanoparticle coated by a copper (II) complex, comprising: forming a mononuclear copper complex by treating a ligand with $Cu^{2+}$ ions; and immobilizing the mononuclear copper complex on $TiO_2$—ZnO nanoparticles to obtain the $TiO_2$—ZnO nanoparticle coated by the copper (II) complex.

Ligand

In one embodiment, the ligand used in the present methods can be 2-((4-hydroxybenzylidene)amino)phenol. In this regard, the ligand can be prepared by condensing 4-hydroxy benzaldehyde with 2-aminophenol in ethanol. Such condensation, in certain embodiments, can take place with refluxing for about 1 to about 3 hours, about 1 hour, about 2 hours, or about 3 hours at a temperature of at least about 80° C., at about 70° C. to about 90° C., or at any temperature therein.

Cu-Complex

In another embodiment, the copper (II) complex, or Cu-complex, can be prepared by providing copper (II) acetate monohydrate in water. The copper (II) acetate monohydrate in water can then be poured into an ethanolic solution containing the ligand at room temperature, followed by refluxing. Such refluxing can take place for about 1 to about 3 hours, about 1 hour, about 2 hours, or about 3 hours. In certain other embodiments, the ligand and $Cu^{2+}$ ions coming from the copper (II) acetate monohydrate are present in a 2:1 stoichiometric ratio.

In this regard, the reaction scheme to obtain the Cu-complex can be identified as follows:

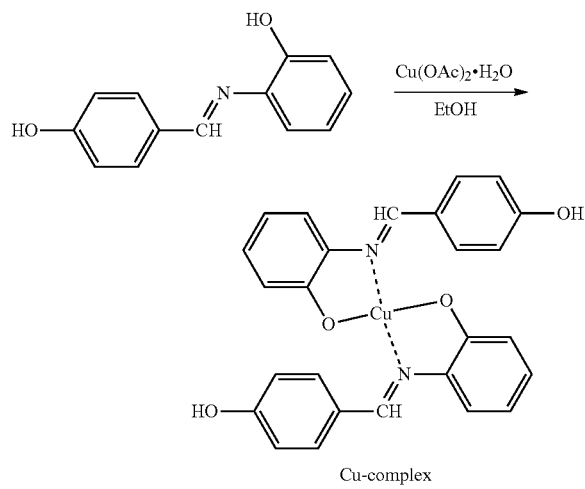

Cu-complex

TiO$_2$—ZnO Nanoparticles

In another embodiment, the TiO$_2$—ZnO nanoparticles can be prepared by making a ZnO nanoparticle solution of *Saussurea costus* and Zn(NO$_3$)$_2$·6H$_2$O. In this regard, the *Saussurea costus* used to extract the TiO$_2$ nanoparticles can be obtained from *Saussurea costus* roots, for example, those available in Al-Ahsa, Saudi Arabia.

In a further embodiment, once the ZnO nanoparticle solution is prepared, the pH of the solution is adjusted to about 10 by adding a base, such as, for example, KOH. The resultant mixture can be stirred for about 1 to about 3 hours, about 1 hour, about 2 hours, or about 3 hours at a temperature of at least about 70° C., at about 70° C. to about 90° C., at about 70° C. to about 80° C., or at any temperature therein.

Likewise, in certain embodiments, a TiO$_2$ solution can be prepared by ultrasonication of TiO$_2$ in ethanol; and then adding this TiO$_2$ solution to the ZnO nanoparticle solution to obtain a mixture. In this regard, the TiO$_2$ solution can be added dropwise to the ZnO nanoparticle solution. The TiO$_2$—ZnO solution can then be filtered to obtain a precipitate from the mixture and the precipitate can be calcined for about 1 to about 3 hours, about 1 hour, about 2 hours, or about 3 hours in a furnace at about 225° C., at about 250° C., at about 275° C., at about 225° C. to about 275° C., or at any temperature therein to obtain TiO$_2$—ZnO nanoparticles.

Immobilization of Cu-Complex on TiO$_2$—ZnO

In further embodiments, immobilizing the Cu-complex on the TiO$_2$—ZnO nanoparticles can be accomplished by refluxing the copper complex in acetonitrile with the TiO$_2$—ZnO nanoparticles in acetonitrile in an ultrasonic bath at a temperature of at least about 70° C., at about 70° C. to about 90° C., at about 70° C. to about 80° C., or at any temperature therein for about 24 hours. This can obtain a dark-gray suspension, which is then filtered to extract the product of the immobilized mononuclear copper complex on TiO$_2$—ZnO nanoparticles.

In this regard, the TiO$_2$—ZnO nanoparticle coated by a copper (II) complex is prepared such that it has a ZnO core surrounded by the TiO$_2$, wherein the copper (II) complex is immobilized on the TiO$_2$.

Methods of Catalytic Oxidation

In an embodiment, the present subject matter may relate to using these Cu-complex on TiO$_2$—ZnO nanoparticles to optimize catalytic efficiency.

In this regard, in an embodiment, the present subject matter relates to a method of catalyzing oxidation of an alcohol, the method comprising: contacting the TiO$_2$—ZnO nanoparticle coated by a copper (II) complex with the alcohol in the presence of aqueous H$_2$O$_2$ or tBuOOH; and obtaining a corresponding aldehyde and acid. In certain embodiments, the alcohol is benzyl alcohol, the aldehyde is benzaldehyde, and the acid is benzoic acid, wherein a yield of the benzaldehyde of at least 90% is obtained. In further embodiments, the yield of the benzaldehyde is about 92% to about 94%. This shows an effective catalytic oxidation of the benzyl alcohol to the selective product with a lower reaction time and temperature than with other, previous catalysts.

In certain other embodiments, the present subject matter relates to a method of catalyzing decarboxylative bromination of an acid, the method comprising: contacting the TiO$_2$—ZnO nanoparticle coated by a copper (II) complex with the acid and a bromide in the presence of aqueous H$_2$O$_2$ or tBuOOH; and obtaining a corresponding decarboxylated acid. In certain embodiments, the acid is α,β-cinnamic acid, the bromide is potassium bromide, and the corresponding decarboxylate acid is 2-bromovinyl benzene, wherein a yield of the 2-bromovinyl benzene of at least 90% is obtained. In further embodiments, the yield of the 2-bromovinyl benzene is about 94% to about 95%. This shows an effective catalytic decarboxylation of the α,β-cinnamic acid to the selective product with a lower reaction temperature under green conditions than with other, previous catalysts.

The present teachings are illustrated by the following examples.

EXAMPLES

Example 1

Ligand Preparation

The Schiff base ligand, 2-((4-hydroxybenzylidene)amino)phenol was prepared by a condensation of 4-hydroxy benzaldehyde with 2-aminophenol (0.12 g and 0.11 g as 1.0 mmol of each reagent) in ethanol (25 mL) with reflux for 2 h at 80° C.

At 400.6 MHz, $^1$H NMR (δ) of the 2-((4-hydroxybenzylidene)amino)phenol ligand: 6.81 (1H, s), 6.89 (2H, d, 3J=4.2 Hz), 6.93 (3H, d, 3J=7.0 Hz), 7.04 (1H, s), 7.14 (1H, s), 7.76 (1H, d, 3J=6.9 Hz), 7.87 (1H, d, 3J=3.8 Hz) 8.55 (1H, CH═N, s) and 9.79 ppm (1H, OH, s), as given in FIG. 1A.

Figure 1B:
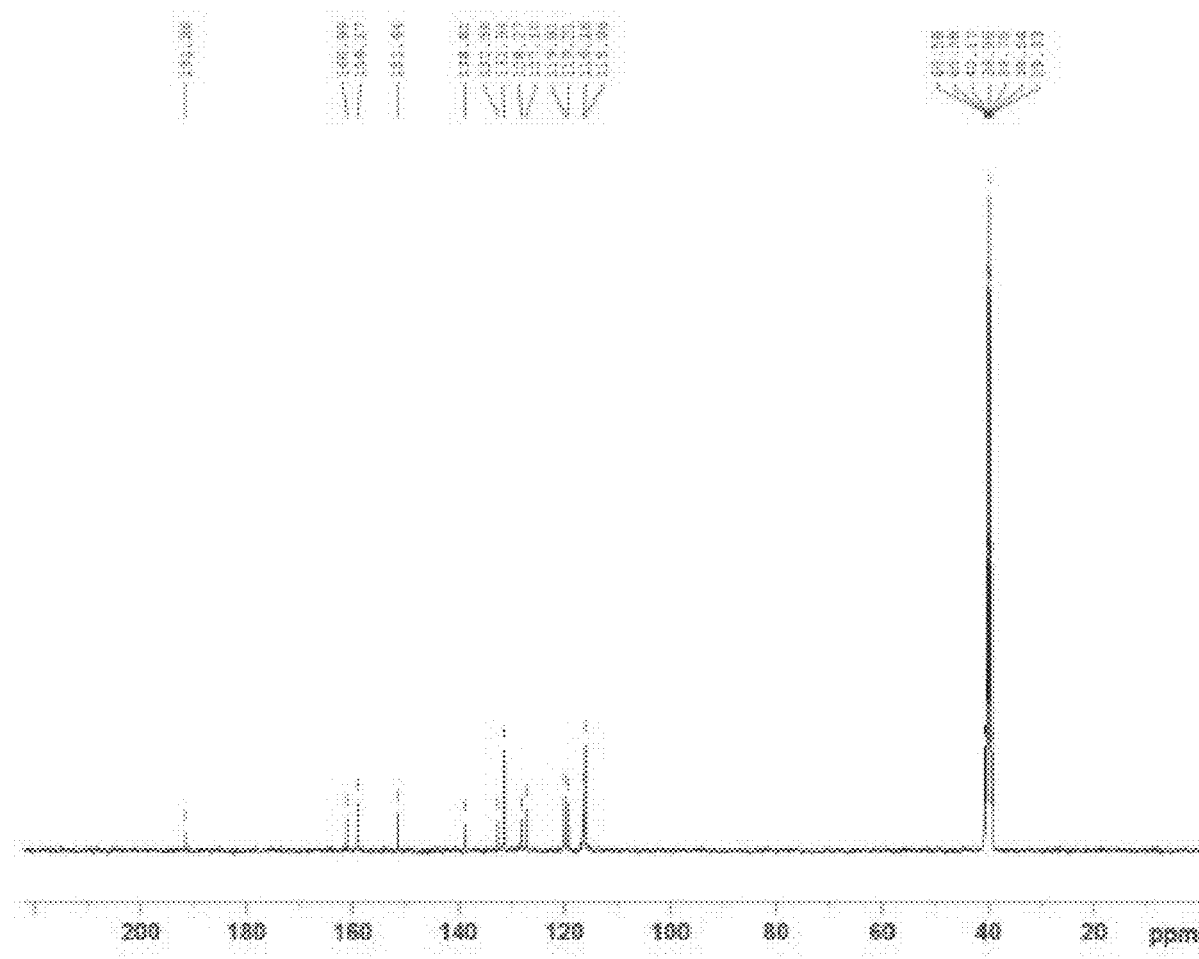
FIG. 1B is a $^{13}$CNMR spectra of the Schiff base ligand 2-((4-hydroxybenzylidene)amino)phenol in DMSO-d6 at 25° C.
Figure 2:
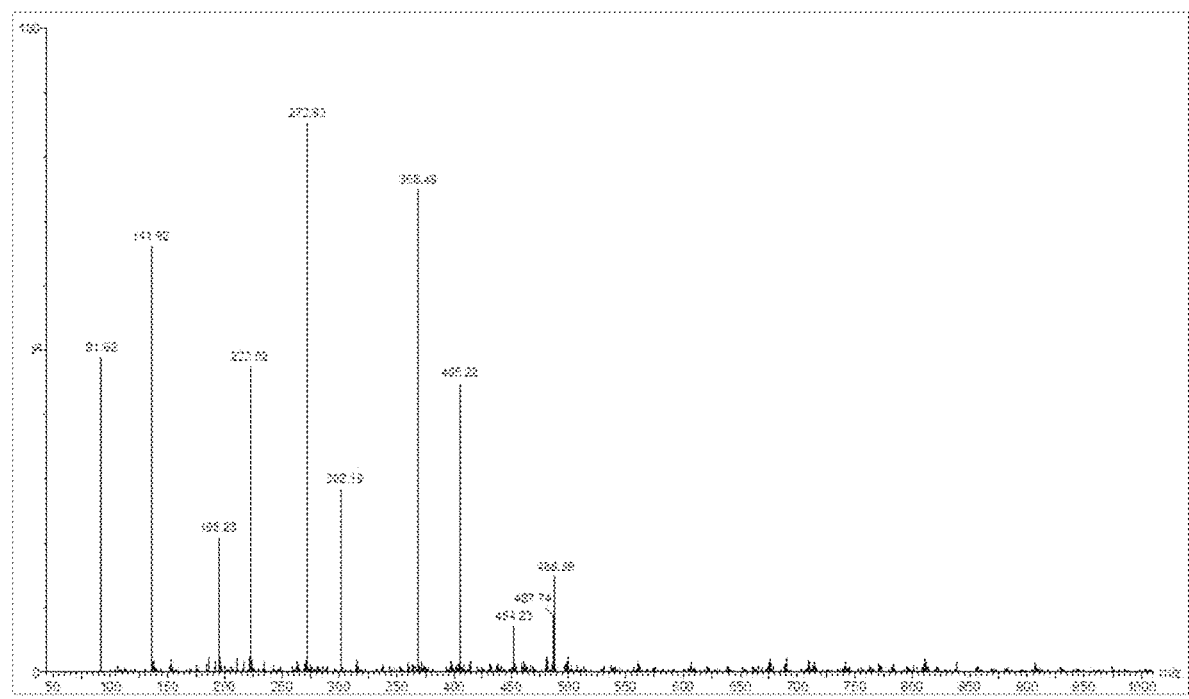
FIG. 2 shows EI-Mass spectra of the Cu-complex in DMF media at 25° C.

At 100.1 MHz, $^{13}$C NMR (δ) of the 2-((4-hydroxybenzylidene)amino)phenol ligand: 115.96, 116.16, 119.21, 119.91, 127.10, 128.27, 131.34, 132.58, 138.82, 151.44, 159.17, 160.99 and 191.36 ppm (CH═N), as given in FIG. 1B.

Example 2

Synthesis of Cu-Complex

Copper (II) acetate monohydrate (0.19 g, 1.0 mmol) in 30 mL H$_2$O was poured into an ethanolic solution (10 mL) of 0.21 g of the ligand (N-((4-hydroxybenzylidene)amino)phenol) (1.0 mmol) at room temperature. Then, the resultant mixture was refluxed for 2 h. Monitoring of the reaction completion was accomplished by TLC to give the final product.

Example 3

Preparation of $TiO_2$—ZnO

First, the ZnO nanoparticles solution was prepared with 20 ml *Saussurea costus*, obtained from *Saussurea costus* roots from the local market in Al-Ahsa, Saudi Arabia, 80 mL of 0.2 mol·dm$^{-3}$ $Zn(NO_3)_2$·$6H_2O$ as a precursor. Then, the pH of the mixture was adjusted to 10 by adding KOH. The resultant mixture was vigorously stirred at 1000 rpm for 2 h at 70-80° C. $TiO_2$ solution was prepared by ultrasonication of 5.0 g of $TiO_2$ in 100 mL ethanol for 15 min and then it was added to ZnO solution dropwise with continuous stirring overnight. Finally, the solution was filtered and rinsed with distilled water several times and left to dry overnight. The precipitate was calcined in a furnace at 250° C. for 2 h to obtain $TiO_2$—ZnO nanocomposite.

Example 4

Immobilization of Cu-Complex on $TiO_2$—ZnO

Immobilization of the Cu-complex on $TiO_2$—ZnO nanocomposites was accomplished under refluxing of the Cu-complex (0.2 g in acetonitrile, 50 mL) with $TiO_2$—ZnO (0.2 g in 50 mL acetonitrile) in an ultrasonic bath at 80° C. for 24 h (~20 kHz). The suspension color of the $TiO_2$—ZnO changed to dark-gray. By filtration, the product of the immobilized Cu-complex on $TiO_2$—ZnO was extracted.

Example 5

Structural Confirmations

The Schiff base ligand and its Cu-complex were characterized by IR, electronic and mass spectra and NMR spectra only for the ligand. The purity of the ligand and the Cu-complex was tested by the micro-elemental analyses of CHN elements and compared to the theoretical values of their suggested chemical structures (with differences less than 0.4%), as given in Table 1. Due to the paramagnetic feature of the Cu-complex, the magnetic moment was measured to give 2.21 B.M. assigning the $d^9$ electronic configuration of the divalent copper ion in its complex with d-d splitting orbitals.

TABLE 1

| Comp. (M.W.) | CHN analyses, % | | | Electronic spectra | | |
|---|---|---|---|---|---|---|
| | C | H | N | $\lambda_{max}$, nm | $\varepsilon$, mol$^{-1}$·cm$^{-1}$ | Assign. |
| Ligand (213.24 g·mol$^{-1}$) | 73.23 (72.98) | 5.20 (5.47) | 6.57 (6.33) | 289 350 434 | 10411 7101 3959 | π→π* n→π* L→CT |
| Cu-complex (488.00 g·mol$^{-1}$) | 63.99 (64.10) | 4.13 (4.23) | 5.74 (5.93) | 280 411 518 | 9058 4596 2007 | π→π* L→MCT d→d |

Table 1 shows the CHN percentage analyses of the Schiff base ligand and Cu-complex. The electronic spectra of $1.0 \times 10^{-5}$ mol dm$^{-3}$ a solution of both compounds in DMF, and their corresponded FTIR spectra at 25° C.

UV and Vis. Spectra

Figure 3:
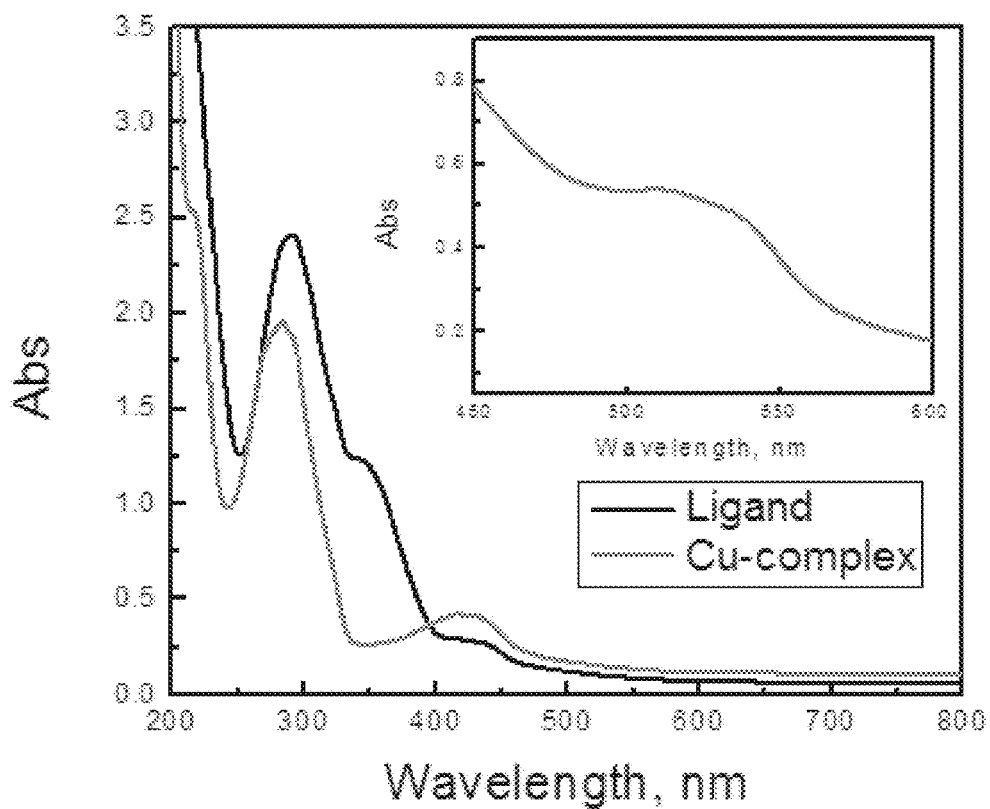
FIG. 3 shows comparable UV-Vis. spectra of the DMF solutions of the Schiff base ligand 2-((4-hydroxybenzylidene)amino)phenol and the Cu-complex at 25° C.

The absorption spectra of the possible electronic transitions for the methanolic solutions of the ligand and the Cu-complex are represented in Table 1 and FIG. 3. At the high-energy region (UV-area), the ligand shows two remarkable bands at 289 and 350 nm for π→π* and n→π* electronic transitions. Indeed, those bands are overlapped in the Cu-complex to be positioned at 280 nm. Furthermore, in the low energy area, the CT (charge transfer) band for the ligand is assigned at 434 nm interpreting the charge transition of the ligand molecule. Moreover, that band is shifted due to the bonding of the ligand to the $Cu^{2+}$ ion in the Cu-complex, which displayed at 411 nm attributing to the charge transfer from the ligand to the metal ion in the Cu-complex (L-MCT). The newly observable band for the d→d transition in the $Cu^{2+}$ ion in its complex, which displayed at 518 nm, referring to the $d_9$ electronic arrangement in the $Cu^{2+}$ ion, as observed in FIG. 3.

IR Spectra

Figure 4:
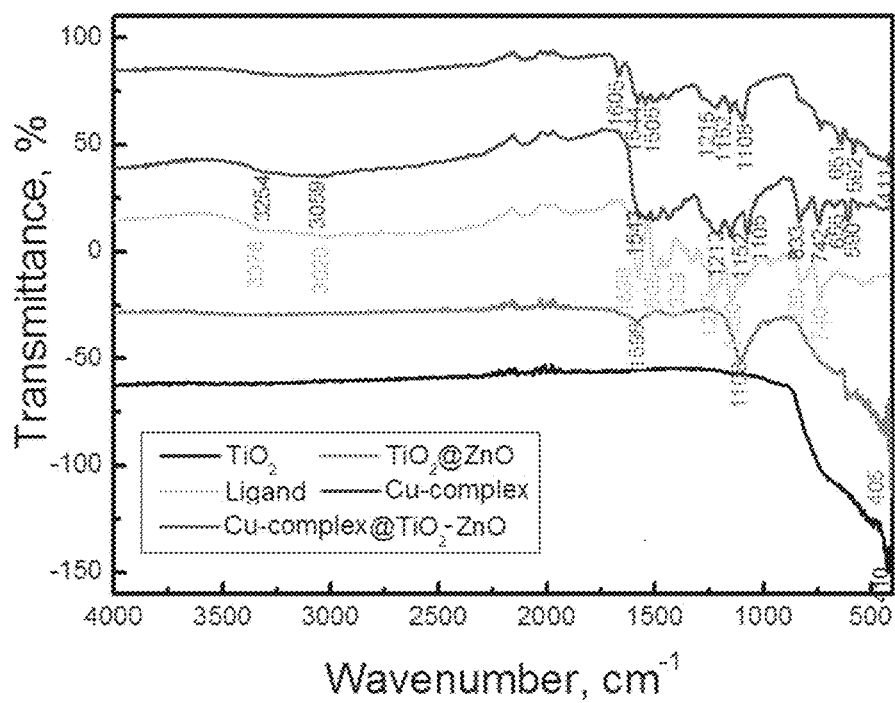
FIG. 4 shows comparable IR spectra for TiO$_2$, TiO$_2$@ZnO, the Schiff base ligand 2-((4-hydroxybenzylidene)amino)phenol, the Cu-complex, and the Cu complex @TiO$_2$—ZnO at 25° C.

FT-IR resonating spectra for the solid phase of the Schiff base ligand and the Cu-complex are represented in FIG. 4. The characteristic bands for both OH groups in the ligand was observed at 3376 cm$^{-1}$, whereas, the CH=N group showed a vibrational band at 1596 cm$^{-1}$. For the Cu-complex, there was an absorption spectral band at 3254 cm$^{-1}$, which corresponded to the p-OH group of the phenolic moiety. Furthermore, a strong shift IR spectral band for the CH=N group, which located at 1543 cm$^{-1}$, was assigned for the sharing of the N-lone pair for the bonding to the $Cu^{2+}$ ion to form the Cu-complex. Two new noted bands were for the complexation of the $Cu^{2+}$ ion to the ligand at 655 and 590 cm$^{-1}$, referring to the stretching vibration of the Cu—O and Cu—N bonding, respectively (Scheme 1).

Considerably, there were additional remarked bands in the IR spectra of the Cu-complex after its successful immobilization on $TiO_2$@ZnO nanoparticles at 1605 and 1108 cm$^{-1}$ (for Zn—O stretching bonding) and at 411 cm$^{-1}$ for Ti—O bonding. The characteristic spectral bands for the Cu-complex were also little influenced by the succeeded supporting binding. The stretching band of the CH=N, Cu—O and Cu—N bonds were located at 1544, 651 and 592 cm$^{-1}$, respectively (FIG. 4).

HRTEM Analysis

FIG. 5A demonstrates the HRTEM image of the $TiO_2$—ZnO nanocomposite, which was composed of small agglomerates and nanoparticles. High magnification HRTEM images of the $TiO_2$—ZnO nanocomposite is shown in FIG. 5B, which obviously proves the irregular spherical nanoparticles of the composite with particle size varying between 46 nm and 128 nm. FIG. 5C exhibits the SEAD pattern with regular circles of different radii which are attributed to crystal orientation planes of the $TiO_2$ and ZnO nanoparticles and indicates the polycrystalline nature of the $TiO_2$—ZnO nanocomposite structure. FIG. 5D illustrates the lattice fringes of 0.31 nm and 0.18 nm match well with the spacing of (101) and (100) planes of anatase $TiO_2$ and wurtzite ZnO crystals, respectively.

Similar results were observed elsewhere for $TiO_2$—ZnO nanocomposite coated by a shell layer of the Cu-complex as shown in FIGS. 6A-D. However, the coated layer of the Cu-complex was characterized by an amorphous structure, then the degree of amorphously enhanced within the Cu complex@$TiO_2$—ZnO compared with the pure $TiO_2$—ZnO nanocomposite. The regular circles (FIG. 6C) which indicates to the crystallite material are turned to light spots (FIG. 6C) attributed to the enhancement of the amorphous structure. Also, FIG. 6D exhibits an image of lattice fringes with d-spacing of 0.35 nm and 0.15 nm of (101) and (100) planes of $TiO_2$ and ZnO crystals, respectively. It can obviously see the amorphous regions beside the crystallite regions.

XRD Analysis

Figure 7:
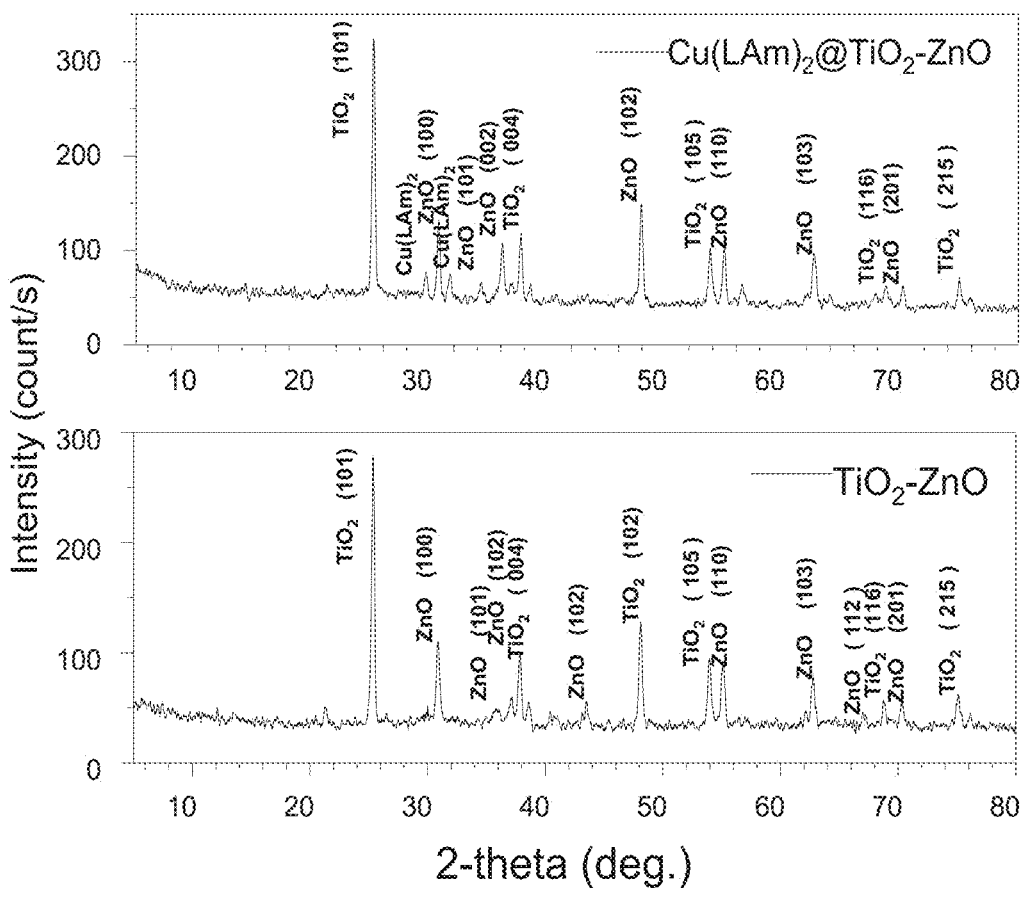
FIG. 7 shows XRD spectrum of the TiO$_2$—ZnO and the Cu-complex@TiO$_2$—ZnO nanocomposites.

FIG. 7 shows XRD spectrum of $TiO_2$—ZnO, and Cu-complex@$TiO_2$—ZnO nanocomposites. In FIG. 7, there are multiple peaks related to two types of crystalline phases of $TiO_2$ (anatase) and ZnO within the nanocomposite. The intense peaks at planes related to $TiO_2$ represented the anatase phase (JCPDS card no. 89-1397). The main peaks at planes correspond to ZnO exhibited the hexagonal wurtzite structure (JCPDS card no. 89-4921). However, as the Cu-complex content coated $TiO_2$—ZnO nanocomposite as shown in FIG. 7, the two weak peaks of ZnO spectrum disappeared at 43.5 and 67 and consequently two planes (102) and (112) are absent due to the major amorphous structure of the shell layer of the Cu-complex coated $TiO_2$—ZnO nanocomposite.

SEM Analysis

Figure 8:
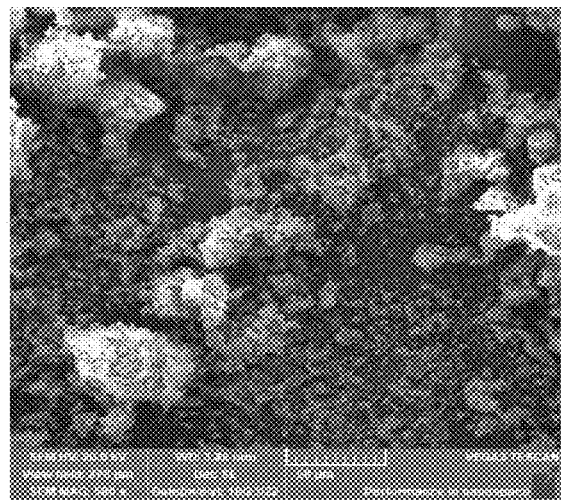
FIGS. 8 & 9 show SEM images of (FIG. 8) TiO$_2$—ZnO, and (FIG. 9) Cu-complex@TiO$_2$—ZnO nanocomposites.
Figure 9:
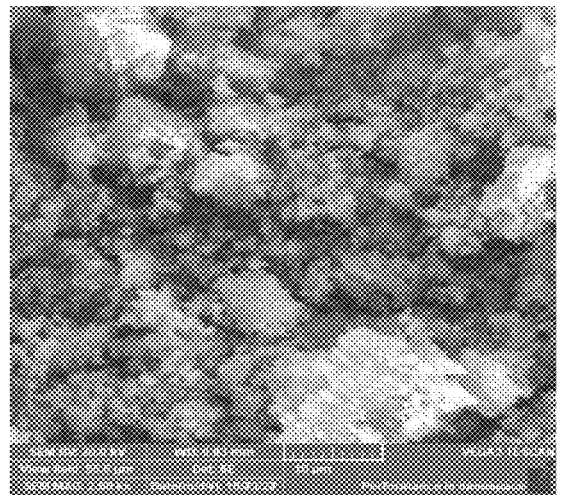

FIGS. 8 and 9 display the SEM images of the $TiO_2$—ZnO, and Cu-complex@$TiO_2$—ZnO nanocomposites. Both SEM images exhibited irregularly shaped aggregates. FIG. 8 of $TiO_2$—ZnO composite shows small agglomerates and nanoparticles with different sizes. On the other hand, the SEM image of the $TiO_2$—ZnO composite coated by the Cu-complex (FIG. 9) displayed a tendency to form more irregularly shaped agglomerates of nanoparticles. The smaller size particles with irregularly shaped agglomerates expectantly upgrade the area of heterogeneous surfaces, which in would be beneficial to enhance the catalytic activity of the $TiO_2$—ZnO nanocomposite.

Based on the IR, XRD, SEM and TEM investigations, it could be inferred that the $TiO_2$—ZnO nanocomposite were successfully coated with the Cu-complex framework, forming Cu-complex@$TiO_2$—ZnO as a core-shell heterojunction catalyst with higher catalytic activity.

Example 6

Catalytic Oxidation Process of Benzyl Alcohol

To evaluate the catalytic efficiency of the Cu-complex on the $TiO_2$—ZnO, the oxidation of benzyl alcohol was studied using $H_2O_2$ and tBuOOH at 50° C. with various reaction times in acetonitrile, homogeneously and heterogeneously, respectively, using CG-MS apparatus for the results analyses (Table 2).

TABLE 2

The catalytic oxidation of benzyl alcohol using $H_2O_2$ or tBuOOH with Cu-complex@$TiO_2$-ZnO catalyst as a function of time at 50° C.

| | | | Amount (%) | | | | |
|---|---|---|---|---|---|---|---|
| Entry | Oxidant | Time (h) | Benzyl alc. | Benzaldehyde | Benzoic acid | Side products | Conversion (%) | Selectivity (%) |
| 1 | $H_2O_2$ | 3.5 | 0 | 92 | 6 | 2 | 100 | 92 |
| 2 | tBuOOH | 3 | 0 | 94 | 5 | 1 | 100 | 93 |
| 3 | $H_2O_2$ with ZnO | 5 | 0 | 62 | 23 | 15 | 100 | 62 |
| 4 | $H_2O_2$ with $TiO_2$—ZnO | 5 | 0 | 71 | 19 | 10 | 100 | 71 |

The optimization of the Cu-complex@$TiO_2$—ZnO was reported at 50° C. after 3.5 h with $H_2O_2$ and after 3 h with tBuOOH giving 92 and 94% of benzaldehyde, respectively. This is excellent results for the catalytic oxidation of benzyl alcohol to the selective product with a low reaction temperature and time compared to other catalysts.

Seemingly, ZnO and $TiO_2$ nanoparticles progressed the catalytic action of the Cu-complex$_2$, as an effective catalyst, towards the selective oxidation of benzyl alcohol by $H_2O_2$ or tBuOOH, In a heterogeneous phase of the reaction contents (α,β-cinnamic acid, potassium bromide, hydrogen peroxide and catalyst) in water, the catalytic results are summarized in Table 3. The catalytic protocols were achieved using Br⁻ anion (as KBr) instead of $Br_2$. The optimization of Cu-complex@$TiO_2$—ZnO was reported at room temperature after 50 min with $H_2O_2$ and after the same time with tBuOOH giving 94 and 95% of 2-bromovinyl benzene. This is excellent result for the catalytic decarboxylative bromination of α,β-cinnamic acid to the selective product with low reaction temperature under green conditions compared to known catalysts.

TABLE 3

Decarboxylative bromination of α,β-cinnamic acid by using KBr and aqueous $H_2O_2$ in water, catalyzed by Cu-complex@$TiO_2$—ZnO.

| | | | Amount (%) | | | | |
|---|---|---|---|---|---|---|---|
| Entry | Catalyst + oxidant | Time, min | α,β-cinnnamic acid | 2-bromovinyl) benzene | Side products | Conversion, (%) | Selectivity, (%) |
| 1 | Cu-complex@$TiO_2$-ZnO + $H_2O_2$ | 50 | 0 | 94 | 6 | 100 | 94 |

TABLE 3-continued

Decarboxylative bromination of α,β-cinnamic acid by using KBr and aqueous $H_2O_2$ in water, catalyzed by Cu-complex@$TiO_2$—ZnO.

| Entry | Catalyst + oxidant | Time, min | α,β-cinnnamic acid | 2-bromovinyl) benzene | Side products | Conversion, (%) | Selectivity, (%) |
|---|---|---|---|---|---|---|---|
| | | | Amount (%) | | | | |
| 2 | Cu-complex@$TiO_2$-ZnO + $^t$BuOOH | 50 | 0 | 95 | 5 | 100 | 95 |

It is to be understood that the method of forming Cu-complex@$TiO_2$—ZnO is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A $TiO_2$—ZnO nanoparticle coated with a copper (II) complex prepared by a method comprising:
   forming a mononuclear copper complex by treating a ligand with $Cu^{2+}$ ions; and
   immobilizing the mononuclear copper complex on $TiO_2$—ZnO nanoparticles to obtain the $TiO_2$—ZnO nanoparticle coated with the copper (II) complex.

2. The $TiO_2$—ZnO nanoparticle coated with a copper (II) complex according to claim 1, having a ZnO core surrounded by the $TiO_2$, wherein the copper (II) complex is immobilized on the $TiO_2$.

3. The $TiO_2$—ZnO nanoparticle coated with a copper (II) complex according to claim 1, wherein the ligand and the $Cu^{2+}$ ions are present in a 2:1 stoichiometric ratio.

4. The $TiO_2$—ZnO nanoparticle coated with a copper (II) complex according to claim 1, wherein the ligand is prepared by condensing 4-hydroxy benzaldehyde with 2-aminophenol in ethanol.

5. The $TiO_2$—ZnO nanoparticle coated with a copper (II) complex according to claim 1, wherein the $Cu^{2+}$ ions are obtained by providing copper (II) acetate monohydrate in water.

6. The $TiO_2$—ZnO nanoparticle coated with a copper (II) complex according to claim 1, wherein the copper (II) acetate monohydrate in water is poured into an ethanolic solution containing the ligand at room temperature, followed by refluxing.

7. The $TiO_2$—ZnO nanoparticle coated with a copper (II) complex according to claim 1, wherein the $TiO_2$—ZnO nanoparticles are prepared according to a method comprising:
   preparing a ZnO nanoparticle solution of *Saussurea costus* and $Zn(NO_3)_2 \cdot 6H_2O$;
   adjusting pH of the ZnO nanoparticle solution to about 10 by adding KOH;
   preparing a $TiO_2$ solution by ultrasonication of $TiO_2$ in ethanol;
   adding the $TiO_2$ solution to the ZnO nanoparticle solution to obtain a mixture; and
   obtaining the $TiO_2$—ZnO nanoparticles as a precipitate from the mixture.

8. The $TiO_2$—ZnO nanoparticle coated with a copper (II) complex according to claim 1, wherein the immobilizing step comprises:
   refluxing the mononuclear copper complex in acetonitrile with the $TiO_2$—ZnO nanoparticles in acetonitrile in an ultrasonic bath at about 80° C. for about 24 hours; and
   obtaining immobilized mononuclear copper complex on $TiO_2$—ZnO nanoparticles by filtration.

* * * * *